(12) United States Patent
Gibson et al.

(10) Patent No.: US 6,783,510 B1
(45) Date of Patent: Aug. 31, 2004

(54) STEERABLE CATHETER

(75) Inventors: Charles A. Gibson, Malden, MA (US); Hab Seang, Lowell, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/349,451

(22) Filed: Jul. 8, 1999

(51) Int. Cl.[7] .................... A61M 37/00; A61M 25/01; A61M 25/02; A61M 25/04; A61M 25/06; A61M 25/08; A61M 25/082; A61M 25/085; A61M 25/088; A61M 25/09; A61M 25/095; A61M 25/098

(52) U.S. Cl. ................ 604/95.01; 604/95.04; 604/528

(58) Field of Search .............. 604/164.01, 164.12, 604/164.13, 528, 95.04, 523, 510, 95.01; 600/585, 434, 114, 146

(56) References Cited

U.S. PATENT DOCUMENTS

| 5,372,587 A | * | 12/1994 | Hammerslag et al. |
| 5,383,852 A | * | 1/1995 | Stevens-Wright ........ 604/95.04 |
| 5,399,164 A | * | 3/1995 | Snoke et al. ................ 604/264 |
| 5,462,527 A | | 10/1995 | Stevens-Wright et al. .... 604/95 |
| 5,489,270 A | * | 2/1996 | van Erp |
| 5,611,777 A | | 3/1997 | Bowden et al. ............... 604/95 |

* cited by examiner

*Primary Examiner*—Brian L. Casler
*Assistant Examiner*—Catherine S. Williams
(74) *Attorney, Agent, or Firm*—Darby & Darby

(57) ABSTRACT

A catheter includes a pull wire which extends through two different lumen and attaches to the distal end of the catheter at an off-axis location. By tensioning the pull wire, the catheter can assume various complex curves, depending on the respective lumen through which the pull wire passes.

55 Claims, 2 Drawing Sheets

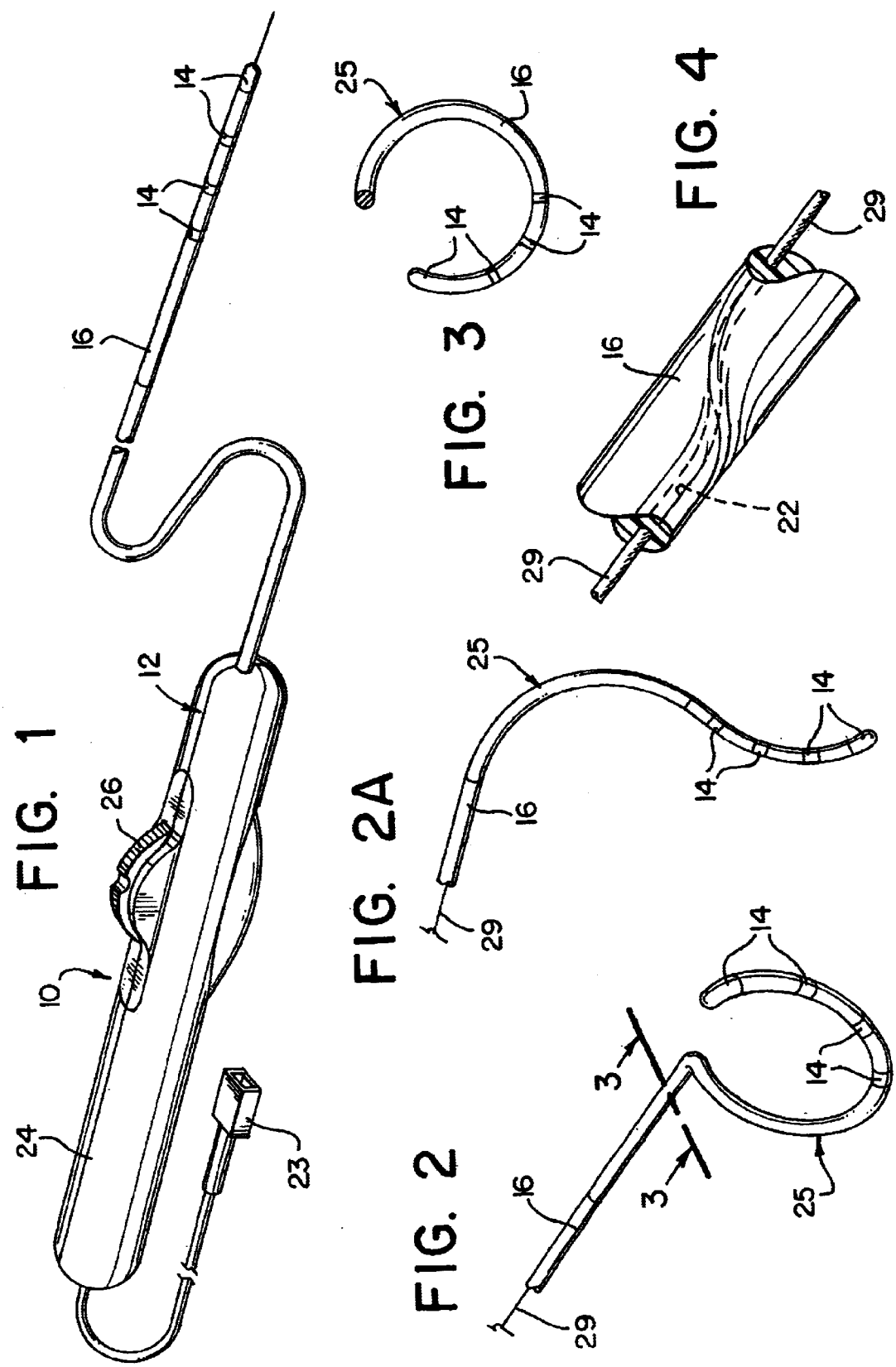

STEERABLE CATHETER

FIELD OF THE INVENTION

The present invention generally relates to the field of steerable catheters. More specifically, the invention is directed to a steerable catheter which includes a single pull wire arranged to allow the catheter to achieve various complex curvatures.

BACKGROUND OF THE INVENTION

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

In order to manipulate the catheter through a patient's vasculature, the catheter must be flexible. In addition, such catheters are preferably steerable, so that the clinician may impart a desired curve to the catheter from a remote location in order to pass through curved areas within a patient. A conventional steerable catheter includes a pull wire which extends through the catheter shaft, and connects to the catheter adjacent the distal end of the catheter at an off-axis location. The pull wire connects to a control knob, slide actuator, or other suitable manipulating member that is mounted in a control handle. A form of such a catheter is disclosed in U.S. Pat. No. 5,383,852 to Stevens-Wright and assigned to the assignee of the rights in the present invention.

While such catheters have gain widespread acceptance in the industry, they nevertheless suffer from certain shortcomings. One shortcoming is that to achieve relatively complex curves, those catheters require multiple pull wires which extend through different lumen and which connect to the catheter at different anchoring points. In addition, the pull wires each require a separate manipulating member to tension the respective pull wires. Thus, in a conventional steerable catheter, a relatively large amount of space is occupied by the steering subsystem, which limits the amount of space available for other components.

In addition, ablation catheters typically must assume various curves so that the ablation electrodes carried on the catheter will come into contact with a patient's tissue at selected locations. Thus, for that additional reason, catheters should be able to assume complex curves.

Accordingly, it will be apparent that there continues to be a need for a steerable catheter which can achieve relatively complex curves to facilitate manipulation of the catheter through a patient's vasculature and to an intended site. Moreover, the needs exists for such a catheter with a steering subsystem that occupies a relatively small amount of space within the catheter. The instant invention addresses these needs.

SUMMARY OF THE INVENTION

Briefly, the present invention is in the form of a catheter that includes a pull wire which extends through two different lumen and attaches to the distal end of the catheter. By tensioning the pull wire, the catheter can assume various complex curves, depending on the different lumen through which the pull wire passes. A proximal segment of the catheter can assume a curve in a first plane, while a distal segment of the catheter can assume a curve in a different plane, thereby achieving a three-dimensional curvature with a single pull wire.

Thus, according to one illustrative embodiment, the present invention is directed to a medical device including an elongated shaft, the shaft being formed with a first lumen extending at least partway through the shaft, and a second lumen extending at least partway through the shaft, the first and second lumen being offset by a predetermined angular distance, the shaft being further formed with a transition region defining a passage leading from the first lumen to the second lumen; a single pull wire extending through the first lumen, the passage in the transition region, and the second lumen; and means for actuating the pull wire to impart a desired curve to the shaft.

In another illustrative embodiment, the invention is directed to a medical device that includes a handle including a pull wire tensioning member, the pull wire tensioning member being manipulable relative to the handle; an elongated shaft connected to the handle, the shaft being formed with a first lumen extending at least partway through the shaft, and a second lumen extending at least partway through the shaft, the first and second lumen being offset by a predetermined angular distance, the shaft being further formed with a transition region defining a passage leading from the first lumen to the second lumen; and a pull wire connected to the tensioning member and extending through the first lumen, the passage in the transition region, and the second lumen.

DESCRIPTION OF THE DRAWINGS

Other objects, features and advantages of the invention discussed in the above summary of the invention will be more clearly understood from the following detailed description of preferred embodiments, which are illustrative only, when taken together with the accompanying drawings in which:

FIG. 1 is a perspective view of a steerable medical device including a steering subsystem according to one illustrative embodiment of the present invention;

FIG. 2 is a partial perspective view of the medical device of FIG. 1 and showing the distal end of the device actuated to assume a first curved configuration according to one illustrative embodiment of the invention;

FIG. 2A is a partial perspective view of the medical device of FIG. 1 and showing the distal end of the device actuated to assume a second curved configuration according to a second illustrative embodiment of the invention;

FIG. 3 is a cross-sectional view taken along the line 3—3 of FIG. 2 and looking in the direction of the arrows;

FIG. 4 is a fragmented, sectional view of the shaft portion of the medical device shown in FIG. 1;

DETAILED DESCRIPTION OF THE PREFERRED EMBODIMENTS

Figure 5:
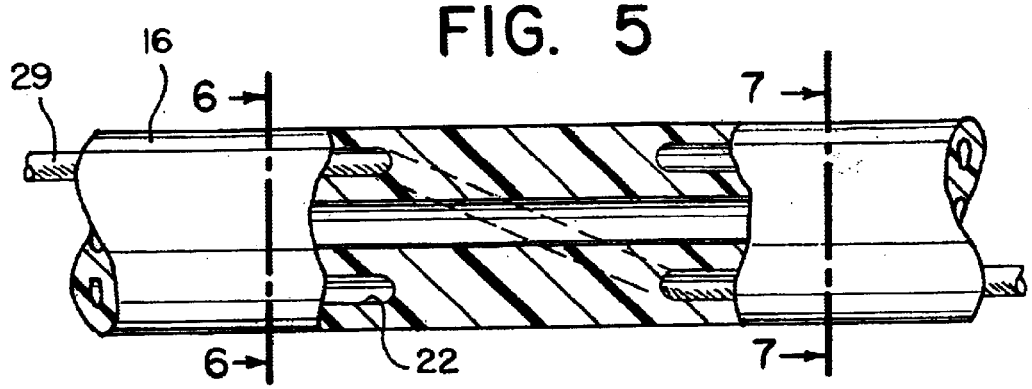
FIG. 5 is a partial sectional view of the shaft portion of the medical device shown in FIG. 1.

Referring now to the drawings, and particularly to FIG. 1, there is shown a medical device 10 according to one illustrative embodiment of the present invention. In one illustrative embodiment, the medical device 10 includes a steering subsystem, generally designated 12, which is operative to impart a desired curve to the catheter. In one illustrative embodiment, the catheter includes one or more electrodes 14, one or more of which may be slidably mounted over an elongated catheter shaft 16 of the device 10 and which are selectively movable relative to the catheter shaft in either a distal or proximal direction along the catheter shaft 16. Thus, for example, in an ablation procedure, the device 10 may be manipulated through a patient's blood vessels by means of the steering subsystem 12 until the electrode 14 is disposed in a desired location within the patient's body. The electrode may then be used for ablation, for sensing electrical activity within the heart, or any other suitable function.

Figure 6:
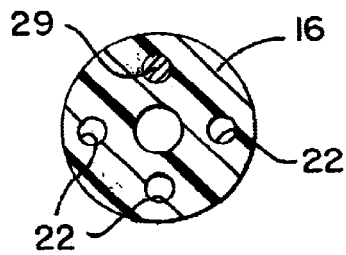
FIG. 6 is a cross-sectional view taken along the line 6—6 of FIG. 5.
Figure 7:
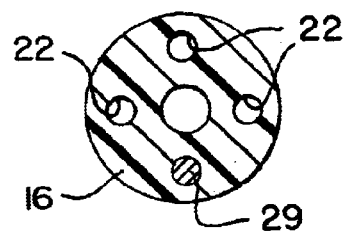
FIG. 7 is a cross-sectional view taken along the line 7—7 of FIG. 5.
Figure 8:
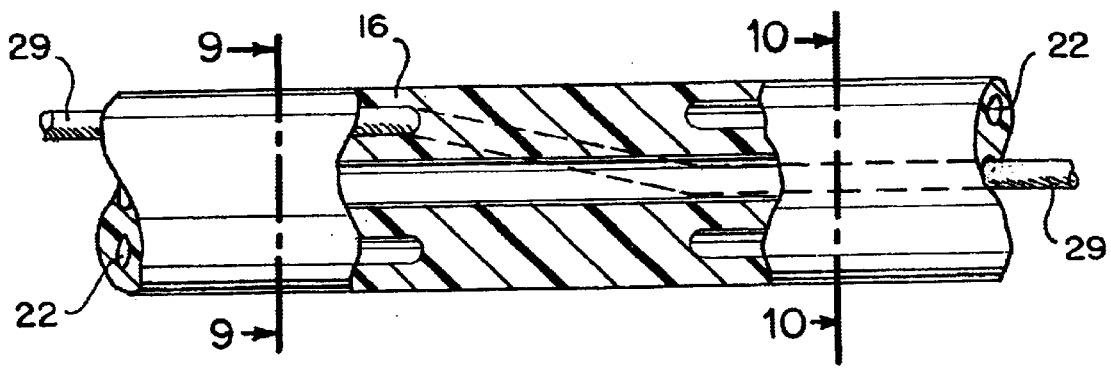
FIG. 8 is a cross-sectional view of another illustrative embodiment of the medical device of FIG. 1.
Figure 9:
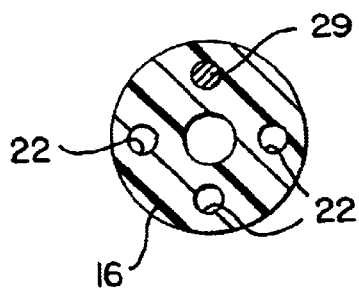
FIG. 9 is a cross-sectional view taken along the line 9—9 of FIG. 8.
Figure 10:
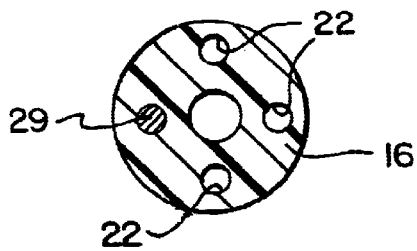
FIG. 10 is a cross-sectional view taken along the line 10—10 of FIG. 8.

Referring to FIG. 1, the medical device 10 in one illustrative embodiment is in the form of a catheter, for example, an ablation catheter, therapeutic catheter, mapping catheter, or other diagnostic catheter. It will be apparent that the medical device 10 of the present invention can take many different forms, such as any medical device having an insertion member to be inserted into a patient's body. In the illustrative embodiment, the catheter includes the catheter shaft 16, which is preferably a flexible shaft which can be manipulated through a patient's blood vessels and to a site of interest within the patient's body, as is described in greater detail below. The catheter shaft defines a plurality of interior lumen 22 (FIGS. 6 and 7) which are formed having predetermined cross-sectional dimensions for passing various components through the respective lumen, as is described in greater detail below.

In one embodiment, the medical device 10 includes a control handle 24 for manipulating the steering subsystem 12 (FIG. 1). The catheter handle may take many different forms. One suitable form of control handle is shown in FIG. 1 and is disclosed in greater detail in U.S. Pat. No. 5,462,527 to Stevens-Wright, the disclosure of which is hereby expressly incorporated by reference as if fully set forth herein. Briefly, the control handle includes a control knob 26 which is rotatable relative to the handle. The control knob is preferably connected to a component of the steering subsystem 12, as is described in greater detail below. Another suitable form of control handle is disclosed in U.S. Pat. No. 5,611,777 to Bowden et al., which is expressly incorporated herein by reference.

The control handle 24 is preferably connected to a connector 23, which connects to a suitable power supply (not shown) to provide ablation energy to the slidable electrode 14, and to diagnostic equipment (not shown) to transmit sensing signals generated by the catheter electrodes, as is well known in the art and described in greater detail below.

According to one illustrative embodiment of the invention, the control knob 26 is engaged to one end of a pull wire 29 which extends through at least two lumens 22 and 22' in the catheter shaft 16 and is connected to the distal end portion of the catheter at an off-axis location. As such, tension applied to the pull wire causes the catheter shaft to curve in a predetermined direction or directions, as is shown in FIGS. 2, 2A, and 3, and is described in greater detail below.

Referring to FIGS. 2A and 5 through 7, there is shown one illustrative embodiment of the medical device 10 of the invention. The single pull wire 29 extends from the control knob 26 through a first lumen 22 to a transition region 25 within the shaft 16. In the transition region, the pull wire transitions to a second lumen 22' which is angularly spaced 180° from the first lumen. The pull wire then extends through the second lumen toward the distal end of the catheter, and connects to the catheter at an off-axis location.

Thus, when tension is applied to the pull wire 29, the proximal region will curve in a first direction and the distal region will curve in the opposite direction (i.e., the two curves lie in the same plane but face in directions 180° apart) (FIG. 2A).

Preferably, the proximal and distal portions of the catheter shaft 16 separated by the transition region 25 are formed of different compositions having different durometers, which allows for different curves for the respective regions from the single pull wire 29. Thus, when tension is created in the pull wire 29, the portion formed of softer material will curve to a greater extent than the more rigid portion. As such, by selecting the durometers of the proximal and distal portions, the extent to which the respective portions curve can be determined. In addition, the catheter shaft may be formed of a relatively rigid material up to the proximal portion, such that when the pullwire is tensioned, only the proximal and distal portions of the catheter shaft curve, and the majority of the shaft remains generally linear (FIG. 2A).

Referring now to FIGS. 2, 3, and 8 through 10, there is shown a second illustrative embodiment of the medical device 10 of the invention. In this embodiment, the pull wire 29 extends through a first lumen 22, and then transitions to a second lumen 22' that is angularly spaced 90° from the first lumen. The pull wire then extends through the second lumen and connects to the distal end of the catheter at an off-axis location.

Thus, when tension is applied to the pull wire 29, the proximal segment curves in a first plane, and the distal segment curves in a plane that is orthogonal to the first plane (i.e., shifted 90° from the first plane) (FIGS. 2 and 3). As such, the catheter assumes a three-dimensional configuration with the single pull wire 29.

It will be apparent to those skilled in the art that the pull wire 29 may be extended through lumen that are angularly spaced at some angle other than 90° or 180°. When the pull wire has a 180° transition between the lumen, the corresponding curves are coplanar. However, when the pull wire transition is less than 180°, the corresponding curves are not coplanar, resulting in a three-dimensional configuration for the catheter.

Thus, depending on the desired configuration, the pull wire transition can be any angle, such as 30°, 45°, 60°, or any other angle.

In addition, while in the illustrative embodiments, the pull wire 29 extends through two different lumen 22 and 22', it will be understood by those skilled in the art that the pull wire may extend through three or more lumen, with the catheter shaft including two or more transition regions between the respective lumen. In that manner, the catheter will have three or more different curved regions, which may be coplanar or not, depending on the transition angles between the respective lumen, as described above.

The catheter shaft 16 preferably includes the one or more electrodes 14 disposed at strategically placed locations relative to the respective curved regions, such that when the pull wire is tensioned, the electrodes are deployed into operative positions for contacting a patient's tissue. One or more of the electrodes 14 may be displaceable relative to the catheter shaft by a relatively stiff displacing member in the form of a mandrel (not shown) which includes a first, proximal end securely connected to a second control knob (not shown) or other suitable member formed on the handle 24. The mandrel may be in the form of a shaft, stiff wire, hypotube, or the like, and extends distally from the control knob through the handle 24, through one of the lumens 22, and then extends laterally with respect to the catheter shaft and into engagement with the inside surface of the slidable electrode.

Such a construction is disclosed in detail in U.S. patent application Ser. No. 09/203,922, and now U.S. Pat. No. 6,178,354, the disclosure of which is expressly incorporated herein by reference.

In operation, a clinician inserts the distal end of the catheter shaft 16 into a patient's blood vessels and manipulates the shaft through the vasculature to an intended site. As the catheter is manipulated through the vasculature, the clinician may periodically tension the pull wire 29 to impart the predetermined curvature to the catheter so that it may pass through curved regions within the patient's body (FIGS. 2, 2A, and 3). In addition, once the catheter is disposed at the intended site within the patient, the pull wire 29 may be tensioned so that the catheter shaft 16 assumes the desired curvature, with one or more of the electrodes 14 carried along the catheter shaft being deployed into contact with a patient's tissue for diagnostic, therapeutic, and/or ablative procedures. Once the procedure or procedures are completed, the clinician then removes the catheter from the patient.

Thus, for example, the distal end region of the catheter may be designed so that it assumes a predetermined curve for manipulation purposes through the patient's vasculature, while one or more other catheter shaft regions may be designed so that they assume various curves for electrode deployment purposes and the like.

From the foregoing, it will be apparent to those skilled in the art that the present invention provides a medical device which includes a steering subsystem that facilitates manipulation of the medical device through a patient's vasculature, and which also facilitates deployment of one or more electrodes into contact with a patient's tissue. In addition, the medical device of the present invention includes a steering subsystem which uses a relatively small number of components.

Having thus described preferred embodiments of the present invention, it is to be understood that the above described arrangement and system is merely illustrative of the principles of the present invention, and that other arrangements and systems may be by those skilled in the art without departing from the spirit and scope of the invention as claimed below.

What is claimed is:

1. A catheter comprising:
    an elongated shaft, the shaft having a length and an axis and being formed with a first lumen extending at least partway along an axis parallel to the axis of the shaft, and a second lumen extending at least partway along an axis parallel to the axis of the shaft, the first lumen and second lumen occupying separate regions along the length of the shaft and being offset by a predetermined angular distance, the shaft being further formed with a transition region defining a passage leading from the first lumen to the second lumen;
    a pull wire extending through the first lumen, the passage in the transition region, and the second lumen; and
    means for actuating the pull wire in one direction to both bend one of the regions in a first direction and another of the regions in a second direction that is different from the first direction.

2. A catheter comprising:
    an elongated shaft, the shaft being formed with a first lumen extending at least partway through the shaft, and a second lumen extending at least partway through the shaft, the first and second lumen being offset by a predetermined angular distance, the shaft being further formed with a transition region defining a passage leading from the first lumen to the second lumen;
    a pull wire extending through the first lumen, the passage in the transition region and the second lumen; and
    means for actuating the pull wire to impart a desired curve to the shaft, wherein the first and second lumen are offset by an angle of 90 degrees.

3. The catheter of claim 1, wherein the first and second lumen are offset by an angle of 180 degrees.

4. A catheter comprising:
    an elongated shaft, the shaft being formed with a first lumen extending at least partway through the shaft, and a second lumen extending at least partway through the shaft, the first and second lumen being offset by a predetermined angular distance, the shaft being further formed with a transition region defining a passage leading from the first lumen to the second lumen;
    a pull wire extending through the first lumen, the passage in the transition region and the second lumen; and
    means for actuating the pull wire to impart a desired curve to the shaft, wherein the first and second lumen are offset by an angle of less than 180 degrees.

5. The catheter of claim 1, wherein the first and second lumen extend along the length of the shaft.

6. The catheter of claim 1, wherein the means for actuating comprises a handle and a pull wire tensioning member mounted to the handle, wherein the tensioning member is manipulable relative to the handle, and wherein the pull wire is connected to the tensioning member, such that manipulation of the tensioning member tensions the pull wire and causes the shaft to assume a predetermined curve.

7. A medical device comprising:
    a handle including a pull wire tensioning member, the pull wire tensioning member being manipulable relative to the handle;
    an elongated shaft connected to the handle, the shaft having a length and an axis and being formed with a first lumen extending at least partway along an axis parallel to the axis of the shaft, and a second lumen extending at least partway along an axis parallel to the axis of the shaft, the first lumen and second lumen occupying separate regions along the length of the shaft and being offset by a predetermined angular distance, the shaft being further formed with a transition region defining a passage leading from the first lumen to the second lumen; and
    a pull wire connected to the tensioning member and extending through the first lumen, the passage in the transition region, and the second lumen;
    whereby tensioning the pull wire in one direction both bends one of the regions in a first direction and another of the regions in a second direction that is different from the first direction.

8. A medical device comprising:
    a handle including a pull wire tensioning member, the pull wire tensioning member being manipulable relative to the handle;

an elongated shaft connected to the handle, the shaft being formed with a first lumen extending at least partway through the shaft, and a second lumen extending at least partway through the shall, the first and second lumen being offset by a predetermined angular distance, the shaft being further formed with a transition region defining a passage leading from the first lumen to the second lumen; and a pull wire connected to the tensioning member and extending through the first lumen, the passage in the transition region, and the second lumen, wherein the first and second lumen are offset by an angle of 90 degrees.

9. The catheter of claim 7, wherein the first and second lumen are offset by an angle of 180 degrees.

10. A medical device comprising:

a handle including a pull wire tensioning member, the pull wire tensioning member being manipulable relative to the handle;

an elongated shaft connected to the handle, the shaft being formed with a first lumen extending at least partway through the shaft, and a second lumen extending at least partway through the shaft, the first and second lumen being offset by a predetermined angular distance, the shaft being further formed with a transition region defining a passage leading from the first lumen to the second lumen; and a pull wire connected to the tensioning member and extending through the first lumen, the passage in the transition region, and the second lumen, wherein the first and second lumen are offset by an angle of less than 180 degrees.

11. The catheter of claims 7, wherein the first and second lumen extend along the length of the shaft.

12. A medical device comprising:

an elongated shaft, the shaft having a length and an axis and being formed with a first lumen extending at least partway along an axis parallel to the axis of the shaft, and a second lumen extending at least partway along an axis parallel to the axis of the shaft, the first lumen and second lumen occupying separate regions along the length of the shaft and being offset by a predetermined angular distance, the shaft being further formed with a transition region defining a passage leading from the first lumen to the second lumen;

a pull wire extending through the first lumen, the passage in the transition region, and the second lumen; and a pull wire tensioning member for actuating the pull wire in one direction to both bend one of the regions in a first direction and another of the regions in a second direction that is different from the first direction.

13. A medical device comprising:

an elongated shaft, the shaft being formed with a first lumen extending at least partway through the shaft, and a second lumen extending at least partway through the shaft, the first and second lumen being offset by a predetermined angular distance, the shaft being further formed with a transition region defining a passage leading from the first lumen to the second lumen;

a pull wire extending through the first lumen, the passage in the transition region, and the second lumen; and a pull wire tensioning member for actuating the pull wire to impart a desired curve to the shaft, wherein the first and second lumen are offset by an angle of 90 degrees.

14. The catheter of claim 12, wherein the first and second lumen are offset by an angle of 180 degrees.

15. A medical device comprising:

an elongated shaft, the shaft being formed with a first lumen extending at least partway through the shaft, and a second lumen extending at least partway through the shaft, the first and second lumen being offset by a predetermined angular distance, the shaft being further formed with a transition region defining a passage leading from the first lumen to the second lumen;

a pull wire extending through the first lumen, the passage in the transition region, and the second lumen; and a pull wire tensioning member for actuating the pull wire to impart a desired curve to the shaft, wherein the first and second lumen are offset by an angle of less than 180 degrees.

16. The catheter of claim 12, wherein the first and second lumen extend along the length of the shaft.

17. A catheter comprising:

an elongated shaft, the shaft having a length and an axis and being formed with a first lumen extending at least partway along an axis parallel to the axis of the shaft, and a second lumen extending at least partway along an axis parallel to the axis of the shaft, the first lumen and second lumen occupying separate regions along the length of the shaft and being offset by a predetermined angular distance, the shaft being further formed with a transition region defining a passage leading from the first lumen to the second lumen:

a pull wire extending through the first lumen the passage in the transition region, and the second lumen; and means for actuating the pull wire in one direction to bend one of the regions in a first direction and another of the regions in a second direction that is different from the first direction, wherein the first and second lumen are offset by an angle of 90 degrees.

18. A catheter comprising:

an elongated shaft, the shaft having a length and an axis and being formed with a first lumen extending at least partway along an axis parallel to the axis of the shaft, and a second lumen extending at least partway along an axis parallel to the axis of the shaft, the first lumen and second lumen occupying separate regions along the length of the shaft and being offset by a predetermined angular distance, the shaft being further formed with a transition region defining a passage leading from the first lumen to the second lumen;

a pull wire extending through the first lumen, the passage in the transition region, and the second lumen; and means for actuating the pull wire in one direction to bend one of the regions in a first direction and another of the regions in a second direction that is different from the first direction, wherein the first and second lumen are offset by an angle of less than 180 degrees.

19. The catheter of claim 1, wherein a portion of the catheter adjacent the first lumen is formed of a composition having a first durometer, and a portion of the catheter adjacent the second lumen is formed of a composition having a second durometer different from the first durometer.

20. A medical device comprising:

a handle including a pull wire tensioning member, the pull wire tensioning member being manipulable relative to the handle;

an elongated shaft connected to the handle, the shaft having a length and an axis and being formed with a first lumen extending at least partway along an axis parallel to the axis of the shaft, and a second lumen extending at least partway along an axis parallel to the axis of the shaft, the first lumen and second lumen occupying separate regions along the length of the shaft and being offset by a predetermined angular distance, the shaft being further formed with a transition region defining a passage leading from the first lumen to the second lumen; and a pull wire connected to the tensioning member and extending through the first lumen, the passage in the transition region, and the second lumen;

whereby tensioning the pull wire in one direction bends one of the regions in a first direction and another of the regions in a second direction that is different from the first direction, wherein the first and second lumen are offset by an angle of 90 degrees.

21. A medical device comprising:

a handle including a pull wire tensioning member, the pull wire tensioning member being manipulable relative to the handle;

an elongated shaft connected to the handle, the shaft having a length and an axis and being formed with a first lumen extending at least partway alone an axis parallel to the axis of the shaft, and a second lumen extending at least partway along an axis parallel to the axis of the shaft, the first lumen and second lumen occupying separate regions along the length of the shaft and being offset by a predetermined angular distance, the shaft being further formed with a transition region defining a passage leading from the first lumen to the second lumen; and a pull wire connected to the tensioning member and extending through the first lumen, the passage in the transition region, and the second lumen;

whereby tensioning the pull wire in one direction bends one of the regions in a first direction and another of the regions in a second direction that is different from the first direction, wherein the first and second lumen are offset by an angle of less than 180 degrees.

22. The medical device of claim 7, wherein a portion of the catheter adjacent the first lumen is formed of a composition having a first durometer, and a portion of the catheter adjacent the second lumen is formed of a composition having a second durometer different from the first durometer.

23. A medical device comprising:

an elongated shaft, the shaft having a length and an axis and being formed with a first lumen extending at least partway along an axis parallel to the axis of the shaft, and a second lumen extending at least partway along an axis parallel to the axis of the shaft, the first lumen and second lumen occupying separate regions along the length of the shaft and being offset by a predetermined angular distance, the shaft being further formed with a transition region defining a passage leading from the first lumen to the second lumen;

a pull wire extending through the first lumen, the passage in the transition region, and the second lumen; and a pull wire tensioning member for actuating the pull wire in one direction to bend one of the regions in a first direction and another of the regions in a second direction that is different from the first direction, wherein the first and second lumen are offset by an angle of 90 degrees.

24. A medical device comprising:

an elongated shaft, the shaft having a length and an axis and being formed with a first lumen extending at least partway along an axis parallel to the axis of the shaft, and a second lumen extending at least partway along an axis parallel to the axis of the shaft, the first lumen and second lumen occupying separate regions along the length of the shaft and being offset by a predetermined angular distance, the shaft being further formed with a transition region defining a passage leading from the first lumen to the second lumen;

a pull wire extending through the first lumen, the passage in the transition region, and the second lumen; and a pull wire tensioning member for actuating the pull wire in one direction to bend one of the regions in a first direction and another of the regions in a second direction that is different from the first direction, wherein the first and second lumen are offset by an angle of less than 180 degrees.

25. The medical device of claim 12, wherein a portion of the catheter adjacent the first lumen is formed of a composition having a first durometer, and a portion of the catheter adjacent the second lumen is formed of a composition having a second durometer different from the first durometer.

26. A medical device comprising:

an elongated shaft having a proximal end, a distal end and an axis, the shaft being formed with a first lumen extending at least partway generally along an axis parallel to the axis of the shaft and a second lumen extending at least partway generally along an axis parallel to the axis of the shaft, the first lumen and second lumen being offset by a predetermined angular distance, the shaft being further formed with a transition region defining a passage leading from a distal end of the first lumen to a proximal end the second lumen;

a pull wire extending through the first lumen, the passage in the transition region, and the second lumen; and a pull wire tensioner for actuating the pull wire to impart a desired curve to the shaft.

27. A medical device comprising:

an elongated shaft having a proximal end and a distal end, the shaft being formed with a first lumen extending at least partway through the shaft and a second lumen extending at least partway through the shaft, the first and second lumen being offset by a predetermined angular distance, the shaft being further formed with a transition region defining a passage leading from a distal end of the first lumen to a proximal end of the second lumen;

a pull wire extending through the first lumen, the passage in the transition region, and the second lumen; and a pull wire tensioner for actuating the pull wire to impart a desired curve to the shaft;

wherein the first and second lumen are offset by an angle of less than 180 degrees.

28. A medical device comprising:

an elongated shaft having a proximal end, a distal end and an axis, the shaft being formed with a first lumen extending at least partway generally along an axis parallel to the axis of the shaft and a second lumen extending at least partway generally along an axis parallel to the axis of the shaft, the first lumen and second lumen being offset by a predetermined angular distance and at least a portion of the second lumen being located distally to the entirety of the first lumen, the shaft being further formed with a transition region defining a passage leading from the first lumen to the second lumen;

a pull wire extending through the first lumen, the passage in the transition region, and the second lumen; and a pull wire tensioner for actuating the pull wire to impart a desired curve to the shaft.

29. The medical device of claim 28, wherein the entirety of the second lumen is located distally to the entirety of the first lumen.

30. A medical device comprising:

an elongated shaft having a proximal end and a distal end, the shaft being formed with a first lumen extending at least partway through the shaft and a second lumen extending at least partway through the shaft, the first and second lumen being offset by a predetermined angular distance and at least a portion of the second lumen being located distally to the entirety of the first lumen, the shaft being further formed with a transition region defining a passage leading from the first lumen to the second lumen;

a pull wire extending through the first lumen, the passage in the transition region, and the second lumen; and a pull wire tensioner for actuating the pull wire to impart a desired curve to the shaft;

wherein the first and second lumen are offset by an angle of less than 180 degrees.

31. The medical device of claim 28, wherein the entirety of the second lumen is located distally to the entirety of the first lumen.

32. The medical device of claim 26, wherein the first and second lumen are offset by an angle of 180 degrees.

33. The medical device of claim 26, wherein the first and second lumen are offset by an angle of less than 180 degrees.

34. The medical device of claim 26, wherein the first and second lumen are offset by an angle of 90 degrees.

35. The medical device of claim 26, wherein a portion of the shaft adjacent the first lumen is formed of a composition having a first durometer, and a portion of the shaft adjacent the second lumen is formed of a composition having a second durometer different from the first durometer.

36. The medical device of claim 27, wherein the first and second lumen are offset by an angle of 90 degrees.

37. The medical device of claim 27, wherein a portion of the shaft adjacent the first lumen is formed of a composition having a first durometer, and a portion of the shaft adjacent the second lumen is formed of a composition having a second durometer different from the first durometer.

38. The medical device of claim 28, wherein the first and second lumen are offset by an angle of 180 degrees.

39. The medical device of claim 28, wherein the first and second lumen are offset by an angle of less than 180 degrees.

40. The medical device of claim 28, wherein the first and second lumen are offset by an angle of 90 degrees.

41. The medical device of claim 28, wherein a portion of the shaft adjacent the first lumen is formed of a composition having a first durometer, and a portion of the shaft adjacent the second lumen is formed of a composition having a second durometer different from the first durometer.

42. The medical device of claim 30, wherein the first and second lumen are offset by an angle of 90 degrees.

43. The medical device of claim 30, wherein a portion of the shaft adjacent the first lumen is formed of a composition having a first durometer, and a portion of the shaft adjacent the second lumen is formed of a composition having a second durometer different from the first durometer.

44. The catheter of claim 2, wherein a portion of the catheter adjacent the first lumen is formed of a composition having a first durometer, and a portion of the catheter adjacent the second lumen is formed of a composition having a second durometer different from the first durometer.

45. The catheter of claim 4, wherein a portion of the catheter adjacent the first lumen is formed of a composition having a first durometer, and a portion of the catheter adjacent the second lumen is formed of a composition having a second durometer different from the first durometer.

46. The medical device of claim 8, wherein a portion of the shaft adjacent the first lumen is formed of a composition having a first durometer, and a portion of the shaft adjacent the second lumen is formed of a composition having a second durometer different from the first durometer.

47. The medical device of claim 10, wherein a portion of the shaft adjacent the first lumen is formed of a composition having a first durometer, and a portion of the shaft adjacent the second lumen is formed of a composition having a second durometer different from the first durometer.

48. The medical device of claim 13, wherein a portion of the shaft adjacent the first lumen is formed of a composition having a first durometer, and a portion of the shaft adjacent the second lumen is formed of a composition having a second durometer different from the first durometereter.

49. The medical device of claim 15, wherein a portion of the shaft adjacent the first lumen is formed of a composition having a first durometer, and a portion of the shaft adjacent the second lumen is formed of a composition having a second durometer different from the first durometer.

50. The catheter of claim 17, wherein a portion of the catheter adjacent the first lumen is formed of a composition having a first durometer, and a portion of the catheter adjacent the second lumen is formed of a composition having a second durometer different from the first durometer.

51. The catheter of claim 18, wherein a portion of the catheter adjacent the first lumen is formed of a composition having a first durometer, and a portion of the catheter adjacent the second lumen is formed of a composition having a second durometer different from the first durometer.

52. The medical device of claim 20, wherein a portion of the shaft adjacent the first lumen is formed of a composition having a first durometer, and a portion of the shaft adjacent the second lumen is formed of a composition having a second durometer different from the first durometer.

53. The medical device of claim 21, wherein a portion of the shaft adjacent the first lumen is formed of a composition having a first durometer, and a portion of the shaft adjacent the second lumen is formed of a composition having a second durometer different from the first durometer.

54. The medical device of claim 23, wherein a portion of the shaft adjacent the first lumen is formed of a composition having a first durometer, and a portion of the shaft adjacent the second lumen is formed of a composition having a second durometer different from the first durometer.

55. The medical device of claim 24, wherein a portion of the shaft adjacent the first lumen is formed of a composition having a first durometer, and a portion of the shaft adjacent the second lumen is formed of a composition having a second durometer different from the first durometer.

* * * * *